(12) United States Patent
Yanagi

(10) Patent No.: US 10,908,121 B2
(45) Date of Patent: Feb. 2, 2021

(54) MEMBRANE DEVICE, MEASUREMENT DEVICE, AND METHOD FOR PRODUCING MEMBRANE DEVICE

(71) Applicant: Hitachi, Ltd., Tokyo (JP)

(72) Inventor: Itaru Yanagi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 133 days.

(21) Appl. No.: 16/082,431

(22) PCT Filed: Apr. 28, 2016

(86) PCT No.: PCT/JP2016/063320
§ 371 (c)(1),
(2) Date: Sep. 5, 2018

(87) PCT Pub. No.: WO2017/187588
PCT Pub. Date: Nov. 2, 2017

(65) Prior Publication Data
US 2019/0094180 A1  Mar. 28, 2019

(51) Int. Cl.
*G01N 27/447* (2006.01)
*G01N 21/64* (2006.01)
*G01N 33/487* (2006.01)
*H01L 21/02* (2006.01)

(52) U.S. Cl.
CPC ... *G01N 27/44791* (2013.01); *G01N 21/6486* (2013.01); *G01N 33/48728* (2013.01); *H01L 21/02356* (2013.01)

(58) Field of Classification Search
CPC ......... G01N 27/44791; G01N 21/6486; G01N 33/48728; H01L 21/02356
See application file for complete search history.

(56) References Cited

U.S. PATENT DOCUMENTS

2011/0120864 A1  5/2011  Takahashi et al.
2017/0138899 A1  5/2017  Itabashi et al.

FOREIGN PATENT DOCUMENTS

| JP | 2012-26986 A | 2/2012 | |
|---|---|---|---|
| JP | 4868067 B2 * | 2/2012 | ....... G01N 33/48728 |
| JP | 4868067 B2 | 2/2012 | |
| JP | 2015-197385 A | 11/2015 | |
| WO | WO 2012/120852 A1 | 9/2012 | |

OTHER PUBLICATIONS

International Search Report (PCT/ISA/210) issued in PCT Application No. PCT/JP2016/063320 dated Jul. 26, 2016 with English translation (four (4) pages).
(Continued)

Primary Examiner — J. Christopher Ball
(74) Attorney, Agent, or Firm — Crowell & Moring LLP

(57) ABSTRACT

The present invention provides a membrane device having a configuration capable of reducing the frequency of clogging of a sample in a nanopore when the sample passes through the nanopore. In the membrane device according to the present invention, a membrane and a semiconductor layer are stacked on a Si substrate, and an insulating film is formed on a side wall of a through hole included in the semiconductor layer.

13 Claims, 13 Drawing Sheets

(56) References Cited

OTHER PUBLICATIONS

Japanese-language Written Opinion (PCT/ISA/237) issued in PCT Application No. PCT/JP2016/063320 dated Jul. 26, 2016 (four (4) pages).

Yanagi et al., "Fabricating Nanopores with Diameters of Sub-1 nm to 3 nm Using Multilevel Pulse-Voltage Injection", Scientific Reports, vol. 4:5000, May 2014, pp. 1-7.

Yanagi et al., "Fabrication of 3-nm-Thick Si3N4 Membranes for Solid-State Nanopores Using the Poly-Si Sacrificial Layer Process", Scientific Reports, vol. 5:14656, Oct. 2017, pp. 1-13.

* cited by examiner

MEMBRANE DEVICE, MEASUREMENT DEVICE, AND METHOD FOR PRODUCING MEMBRANE DEVICE

TECHNICAL FIELD

The present invention relates to a membrane device.

BACKGROUND ART

A technique using nanopores has been studied as an approach for realizing the next generation DNA sequencer. In this technique, a hole (nanopore) having approximately the same size as the DNA is provided in a thin film (membrane). Chambers are formed above and below the membrane, respectively. The chamber is filled with an aqueous solution. The chamber is provided with an electrode disposed to be in contact with the aqueous solution. DNA to be measured is put into one chamber and is made to electrophoretically pass through the nanopore by applying a potential difference between electrodes. When the DNA passes through the nanopore, an ion current flowing between both electrodes is changed. A structural feature and a base sequence of the DNA are determined by measuring temporal change of the ion current. With this technique, it is possible to measure the structural features of various biomolecules not limited to DNA.

As a method of manufacturing the nanopore device, from the viewpoint of improving the mechanical strength, a method has been attracting attention that uses a semiconductor substrate, a semiconductor material, and a semiconductor process. For example, the membrane can be formed using a silicon nitride film (SiN film). By applying a voltage stress to the membrane in an ionic aqueous solution to cause dielectric breakdown, fine pinholes can be formed in the membrane, and thus nanopores can be formed (refer to NPTL 1). The nanopores can also be formed by etching the membrane with agglomerated electron beams.

As one important factor for determining DNA reading accuracy of the nanopore sequencer, a thickness of the membrane can be exemplified. The interval between the adjacent four kinds of bases arranged in a DNA chain is approximately 0.34 nm. If the membrane thickness is larger than the interval, a plurality of bases simultaneously pass through the nanopore. Then, the ion current at a certain point of time is measured when the plurality of bases simultaneously pass through the nanopore, and thus the accuracy for specifying the bases is deteriorated. This causes the deterioration of the determination accuracy of the base sequence, and analysis of signals becomes more complicated. Even in a case of obtaining the structural features of various biomolecules other than DNA, the thicker the membrane, the lower the spatial resolution as well. Therefore, it is very important to make the thickness of the membrane having nanopores as thin as possible for improving the structure determination accuracy of the object to be measured.

In order to thin the membrane, the surface area of the membrane is preferable to be as narrow as possible. The reason for this is that as the surface area of the membrane is narrow, the probability of inevitable defects (weak spots and pinholes due to bonding defects between atoms) generated at the time of forming the membrane is decreased. In addition, at the time of forming the membrane, it is important as far as possible to avoid a process in which the membrane may be scraped or destroyed. Also, it is important not to damage the membrane as far as possible during the process of forming the membrane.

As a very skillful technique of forming an ultra-thin membrane while paying attention to the above, a technique disclosed in NPTL 2 below has been known. In the same document, a membrane is formed by the following procedure: (1) a SiN film, a poly-Si film, and a SiN film are stacked on a Si substrate in this order, (2) a partial region of the uppermost SiN film is removed by etching, (3) a back surface of the Si substrate is etched by a TMAH liquid, and (4) the poly-Si film is etched with a KOH aqueous solution through a part of the upper SiN film which is partially opened. Through these steps, an ultrathin membrane made of the SiN film can be formed in a small region surrounded by the poly-Si film. This method is very stable as a method of forming the SiN membrane, and it is possible to stably form an ultra-thin membrane having a thickness of about 3 nm at minimum. A sensor that detects DNA and other biomolecules with high sensitivity is completed by forming the nanopores on the membrane.

CITATION LIST

Non Patent Literature

NPTL 1: Yanagi, I., Akahori, R., Hatano, T. & Takeda, K. Fabricating nanopores with diameters of sub-1 nm to 3 nm using multilevel pulse-voltage injection. Sci. Rep. 4, 5000; DOI: 10.1038/5rep05000 (2014).

NPTL 2: Yanagi, I., Ishida, T., Fujisaki, K. & Takeda, K. "Fabrication of 3-nm-thick Si3N4 membranes for solid-state nanopores using the poly-Si sacrificial layer process" Sci. Rep. 5, 14656; doi: 10.1038/srep14656 (2015).

SUMMARY OF INVENTION

Technical Problem

In the nanopore sensor disclosed in NPTL 1, the inventors of the present invention has studied and found that a phenomenon in which DNA is clogged in the nanopore when the DNA passes through the nanopore is observed with high frequency. When the phenomenon in which DNA is clogged in the nanopore frequently occurs during measurement, the throughput of the measurement decreases. Although the clogging of DNA can be resolved by applying a high voltage, application of the high voltage damages the nanopore sensor, resulting in deterioration of the pressure resistance and lifetime of the sensor. There is a case where even if the high voltage is applied, the clogging is not resolved and the nanopore measurement is to be terminated at that point. The measurement cannot be normally performed while DNA is clogged in the nanopore.

The present invention has been made in view of the above problems, and an object of the present invention is to provide a membrane device having a configuration capable of reducing the frequency of clogging of a sample in a nanopore when the sample passes through the nanopore.

Solution to Problem

In the membrane device according to the present invention, a membrane and a semiconductor layer are stacked on a Si substrate, and an insulating film is formed on a side wall of a through hole included in the semiconductor layer.

Advantageous Effects of Invention

According to the membrane device of the present invention, it is possible to reduce the frequency of the clogging of the nanopore when the sample passes through the nanopore.

DESCRIPTION OF EMBODIMENTS

First Embodiment

Figure 1:
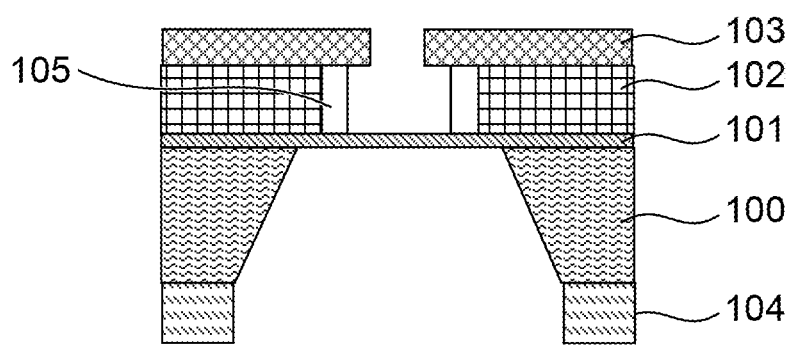
FIG. 1 is a sectional view of a membrane device according to a first embodiment of the present invention.

FIG. 1 is a sectional view of a membrane device according to a first embodiment of the present invention. A SiN film 101, a poly-Si film 102, and a SiN film 103 are stacked in this order on a Si substrate 100. A SiN film 104 is stacked on a back surface of the Si substrate 100. The poly-Si film 102 and the Si substrate 100 each have a hole penetrating to a depth reaching the SiN film 101. The SiN film 101 is disposed so as to separate these holes. Accordingly, a region including only the SiN film 101 exists at the center potion of the SiN film 101. Hereinafter, this region may be referred to as a membrane region in some cases. The side wall surface of the hole included in the poly-Si film 102 is covered by the $SiO_2$ film 105. As for each of the film thicknesses, for example, the SiN film 101 is 3 nm, the poly-Si film 102 is 150 nm, the SiN film 103 is 100 nm, the SiN film 104 is 100 nm, and the $SiO_2$ film 105 is 100 nm.

As a method of manufacturing this device, for example, oxidation of the side wall surface of the poly-Si film 102 of the device manufactured based on the manufacturing method disclosed in NPTL 1 can be exemplified. Examples of the oxidation method include a thermal oxidation method in the oxygen atmosphere. For example, the $SiO_2$ film 105 can be formed by exposing the device to an oxygen atmosphere of about 900° C. to 950° C. for about five to ten hours. At this time, it is very hard to oxidize the SiN film, and thus the oxidation amount of the SiN film 101 is slight. Therefore, the thickness of the SiN film 101 before oxidation and the thickness of the SiN film 101 after oxidation hardly change. That is, the thickness of the SiN film 101 formed in accordance to the manufacturing method disclosed in NPTL 1 is substantially maintained as it is.

Figure 2:
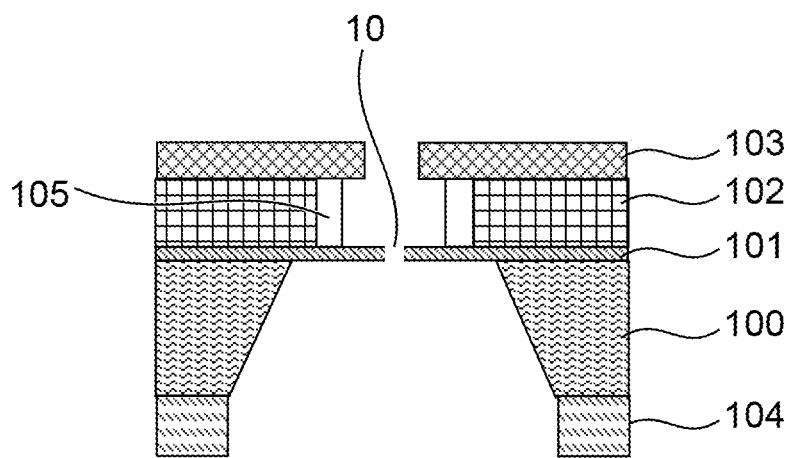
FIG. 2 is a sectional view after forming a nanopore 10 in the membrane device of FIG. 1.

FIG. 2 is a sectional view after forming a nanopore 10 in the membrane device of FIG. 1. As the method of forming nanopore, (1) an electron beam irradiation method using a transmission electron microscope (TEM), (2) a method of forming nanopores 10 by applying a high voltage to a membrane in an aqueous solution, and the like are exemplified. In the latter case, it is desirable to measure the DNA as it is without drying the nanopore 10 after forming the nanopore 10. Therefore, it is typical that a person in charge of DNA measurement forms the nanopore 10. In this case, the nanopore 10 is shipped as a product in a state of the device (FIG. 1) in which the nanopore 10 is not formed. The opening size of the nanopore 10 is desirably 1 to 3 nm for sequencing DNA, for example.

Since the thickness of the SiN film 101 hardly changes after the oxidation of the device and after forming the nanopore 10, the spatial resolution after formation of the nanopore 10 is about the same degree as that of the spatial resolution of the nanopore sensor disclosed in NPT 1.

Figure 3:
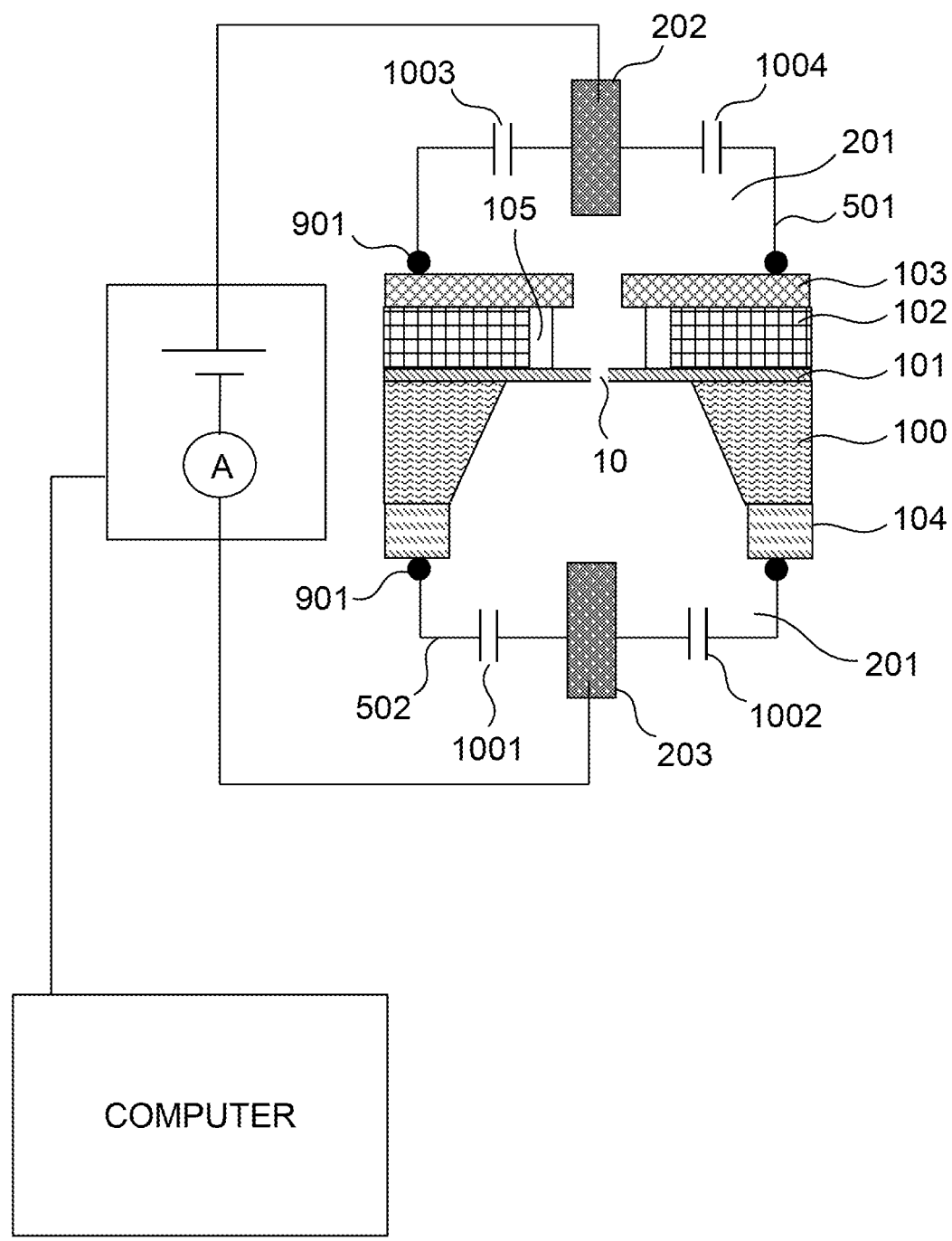
FIG. 3 is a configuration diagram of a measuring device provided with the membrane device illustrated in FIG. 2.

FIG. 3 is a configuration diagram of a measuring device provided with the membrane device illustrated in FIG. 2. Here, an example of the case will be described where the base sequence of DNA is measured by the nanopore 10. The membrane device is close contact with a first chamber 501 and a second chamber 502 via an o-ring 901. The first chamber 501 accommodates holes included in each of the SiN film 103 and the poly-Si film 102 by covering the membrane device from the SiN film 103 side. The second chamber 502 accommodates holes included in each of the Si substrate 100 and the SiN film 104 from the SiN film 104 side.

Each of the chambers is filled with an aqueous solution 201 (for example, a KCl aqueous solution). The aqueous solution is injected and extracted by using inlets (1001 and 1003) and outlets (1002 and 1004). The DNA to be detected is placed in the aqueous solution 201 inside one or both chambers. Electrodes 202 and 203 are, for example, Ag/AgCl electrodes. When a potential difference is provided between the electrodes 202 and 203, the DNA in the aqueous solution 201 is attracted to the nanopore 10 and passes through the nanopore. For example, the DNA present on the second chamber 502 side can pass through the nanopore 10 by setting the potential of the electrode 203 to 0 V and the potential of the electrode 202 to 0.5 V.

The measuring device is equipped with an ammeter for measuring the ion current when the DNA passes through the nanopore 10. A computer receives a measurement result thereof. When the DNA passes through the nanopore 10, the ion current passing through the nanopore is decreased as compared with a case where there is no DNA in the nanopore 10. It is possible to read the base sequence and the structure of the DNA based on the change of an ion current value when the DNA passes through the nanopore.

FIG. 4 is a time trace of the ion current passing through the nanopore 10, measured by using the measuring device illustrated in FIG. 3. There are many phenomena in which the ion current is decreased when the DNA passes through the nanopore 10. The measured DNA has a base number of 60 kb to 10000 kb. In this case, it is typical that the time length from when DNA enters the nanopore 10 to when it goes out is less than 1 second.

Figure 4A:
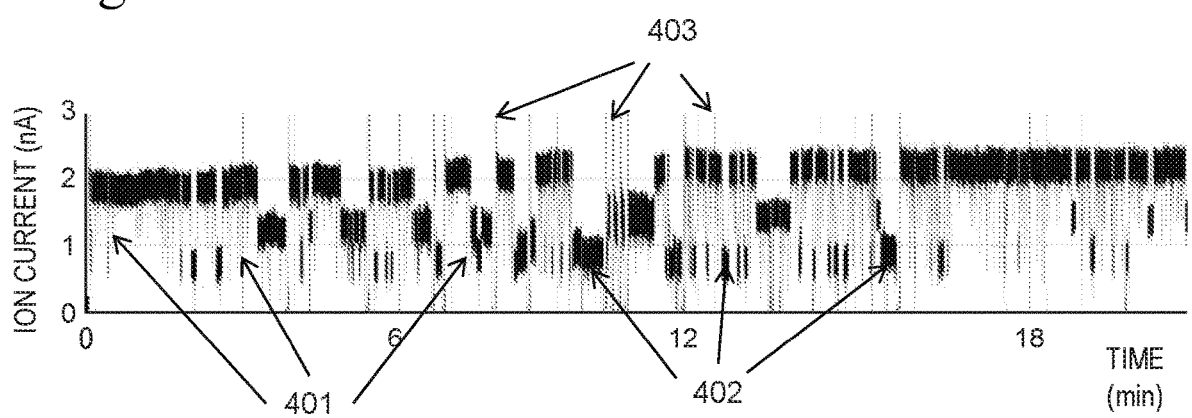
FIGS. 4A and 4B are time traces of the ion current passing through the nanopore 10, measured by using the measuring device illustrated in FIG. 3.

FIG. 4(a) illustrates measurement results using the membrane device which is not provided with the $SiO_2$ film 105 (in which the $SiO_2$ film 105 is removed from the structure in FIG. 2). In addition to a current reduction event 401 which indicates that the DNA normally passes through the nanopore (the DNA passes through the nanopore for 1 second or shorter), a large number of current reduction events 402 for a long time of period of 1 second or longer are also confirmed. The current reduction event 402 during the long time of period is caused by the fact that the DNA is clogged in the nanopore, or that the DNA is caught in a location other than the nanopore and the DNA cannot pass through the nanopore. In the present specification, hereinafter, abnormal current reduction events of 1 second or longer are collectively referred to as a nanopore clogging phenomenon. In order to extract the DNA clogged in the nanopore, it is necessary to apply the high voltage pulse 403; however, the high voltage pulse damages the nanopore and deteriorates the withstand voltage and lifetime of the device, which is not preferable.

Figure 4B:
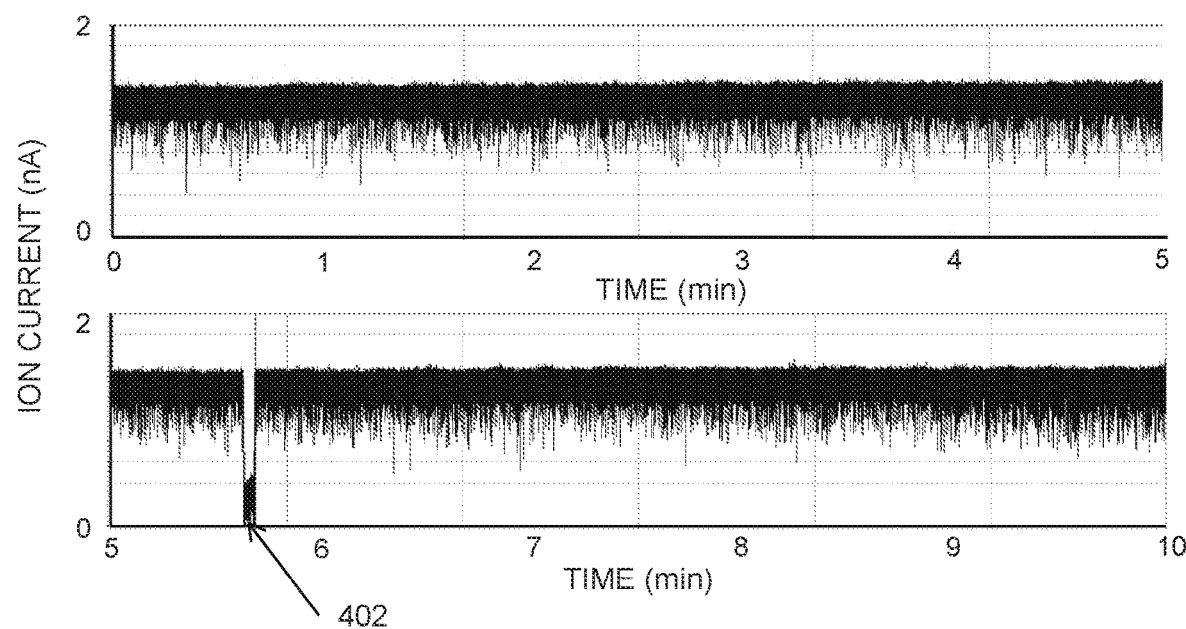

FIG. 4(b) illustrates measured results by using the measuring device according to the first embodiment. As compared with FIG. 4(a), it can be seen that the frequency of the clogging phenomena of nanopores is lower.

The probability of the nanopore clogging phenomenon is defined as (the number of the nanopore clogging phenomena/number of normal DNA passage events for 1 second or shorter). The probability by which the nanopore clogging phenomenon occurs in FIG. 4(a) is 2% to 12%, and the probability by which the same phenomenon occurs in FIG. 4(b) is less than 1%.

From these results, it was found that the frequency of the nanopore clogging phenomenon can be greatly decreased by forming the $SiO_2$ film 105 on the side wall of the poly-Si film 102. Also, these results suggest that a cause of clogging the DNA in the nanopore, or a cause of stagnating the DNA in the nanopore (in summary, a cause of the nanopore clogging phenomenon) was based on an interaction between the poly-Si film 102 (i.e. a semiconductor film) and the DNA, and when the side wall of the poly-Si film 102 was covered with the $SiO_2$ film (i.e. an insulating film), the interaction was relaxed and the nanopore clogging phenomenon was relaxed.

When the frequency of the nanopore clogging phenomenon is decreased, the number of high voltage pulse application for resolving the nanopore clogging phenomenon can be decreased. Therefore, the withstand voltage or the lifetime of the device is not deteriorated so much, and measurement during a longer period of time becomes possible. In addition, when the frequency of the nanopore clogging phenomenon is decreased, the throughput of the measurement is improved. A period during the nanopore clogging phenomenon occurs is unnecessary period of time since a normal current value derived from the base sequence or the structure of the DNA cannot be obtained. Therefore, when the frequency of the nanopore clogging phenomenon is decreased, it leads to improvement of the throughput of measurement.

The thickness of the $SiO_2$ film 105 is preferably 5 nm or more, and is more preferably 10 nm or more. When the thickness of the $SiO_2$ film 105 is 5 nm or more, it is possible to obtain an effect of decreasing the frequency of the nanopore clogging phenomenon. In addition, when the thickness of $SiO_2$ film 105 is 10 nm or more, there is almost no possibility that the $SiO_2$ film 105 is deteriorated in the aqueous solution at the time of the measurement for a long period of time and then the surface of the poly-Si film 102 is exposed.

An amorphous Si film (amorphous Si film) may be used instead of the poly-Si film 102. Specifically, in the method of manufacturing the device disclosed in NPTL 1, a film 102 is formed by using an amorphous Si film, and then the side wall of the film 102 is covered with the $SiO_2$ film 105, thereby the above described effect (that is, an effect that the frequency of the nanopore clogging phenomenon can be greatly decreased) can be sufficiently exerted.

In the manufacturing process disclosed in NPTL 1, at the time of etching the film 102, a film formed of another material can be used instead of the SiN film 103 as long as it is a material in which the etching rate is sufficiently lower than that of the film 102 and thus it is difficult to etch. For example, in NPTL 1, a KOH aqueous solution is used at the time of etching the film 102. As to the KOH aqueous solution, the etching rate of $SiO_2$ is significantly slower than the etching rate of Si, and thus the film 103 may be formed using $SiO_2$.

In the manufacturing process disclosed in NPTL 1, at the time of etching the Si substrate 100, a film formed of another material can be used instead of the SiN film 104 as long as it is a material in which the etching rate is sufficiently lower than that of the Si substrate 100 and thus it is difficult to etch. For example, in a case of using tetramethyl ammonium hydroxide (TMAH) liquid at the time of etching the Si substrate 100, $SiO_2$ having a thickness of about 500 nm can be used as the film 104.

In the manufacturing process disclosed in NPTL 1, the film 101 can also be formed using a material other than SiN as long as it is a material which is not substantially etched at the time of etching the film 102. For example, $HfO_2$, HfAlOx, ZrAlOx, $Ta_2O_5$, SiC, SiCN, a carbon film, and a compound thereof can be exemplified.

First Embodiment: Summary

In the membrane device according to the first embodiment, the nanopore 10 is formed on the ultra-thin membrane (SiN film 101), and thus it has high spatial resolution in extracting structural features such as DNA and various other molecules. In addition, the occurrence of the nanopore clogging phenomenon is less, and thus the measurement throughput is high. Further, the number of high voltage pulse application for resolving the nanopore clogging phenomenon is reduced, and thus the lifetime and breakdown voltage of the device are not deteriorated so much.

Second Embodiment

Figure 5:
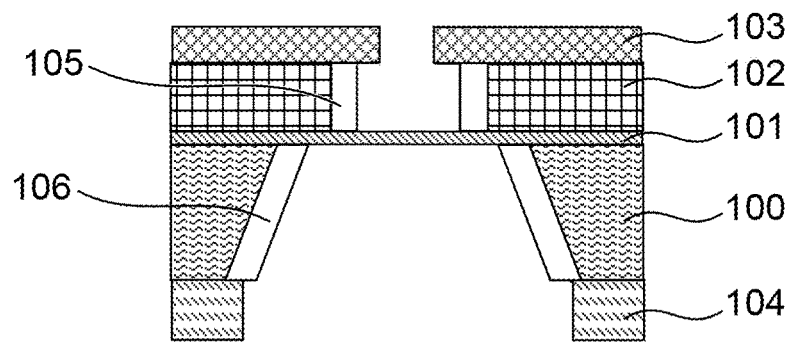
FIG. 5 is a sectional view of a membrane device according to a second embodiment of the present invention.

FIG. 5 is a sectional view of a membrane device according to a second embodiment of the present invention. In the second embodiment, when the side wall of the poly-Si film 102 is subjected to oxidation, the side wall of the Si substrate 100 is concurrently subjected to oxidation so as to form a $SiO_2$ film 106. The thickness of each of the $SiO_2$ films 105 and 106 is, for example, set to be 100 nm. Other configurations are the same as those in the first embodiment.

Figure 6:
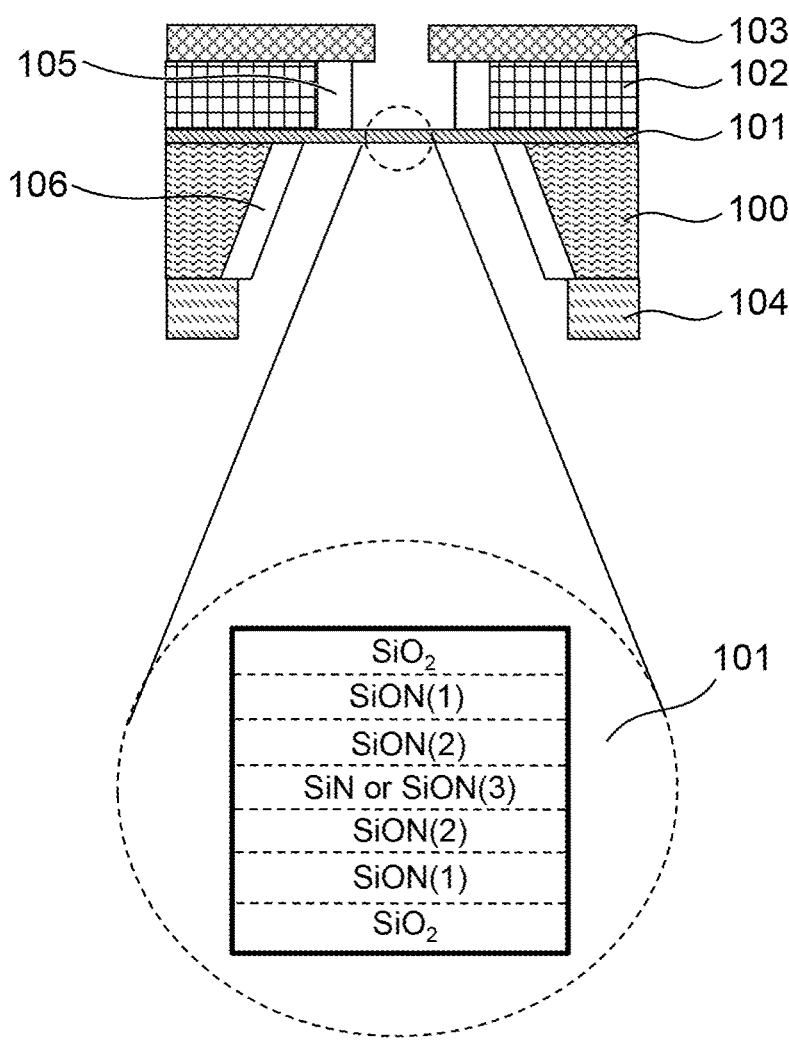
FIG. 6 is a composition example of a SiN film 101 in the second embodiment.

FIG. 6 is a composition example of the SiN film 101 in the second embodiment. When the oxidation is performed at a high temperature (for example, 950° C. or higher) for a long period of time (for example, 10 hours or longer), the SiN film 101 is also subjected to oxidation to some extent. The higher the temperature at the time of the oxidation, or the longer the time of the oxidation, the oxidation amount is increased. The surface layer portion of the SiN film 101 has $SiO_2$ or a composition similar to $SiO_2$, and as it goes from the surface layer portion of the film toward the center in the thickness direction of the film, it has a composition similar to SiN. In FIG. 6, intermediate compositions between SiN and $SiO_2$ are denoted by SiON (1) to SiON (3). The SiON (3) has the composition closest to SiN, the SiON (1) is the composition closest to $SiO_2$, and the SiON (2) is intermediate composition.

Since the SiN film is very hard to oxidize, even if the SiN film 101 has a film composition as illustrated in FIG. 6, there are typically few regions of $SiO_2$ or SiON (1), and most of the regions are SiN or SiN (3). Accordingly, the SiN film 101 maintains its thickness substantially even after oxidation. Therefore, the spatial resolution after forming the nanopore 10 is about the same as the high spatial resolution of the nanopore sensor disclosed in NPTL 1. When the surface layer portion of the SiN film 101 has a composition close to $SiO_2$, the hydrophilicity of the SiN film 101 is improved, so that the contact property with the aqueous solution 201 is further improved. Accordingly, when introducing the aqueous solution 201, it is difficult for bubbles to enter the nanopore 10, and thus the probability of hindering the measurement is decreased.

Figure 7:
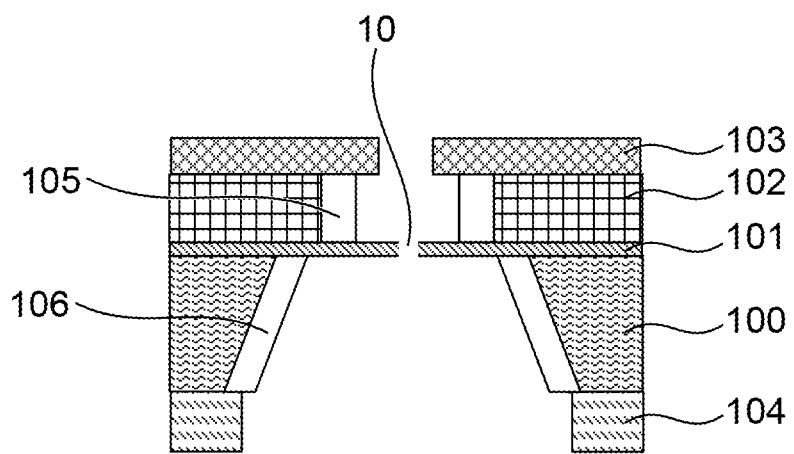
FIG. 7 is a sectional view after forming a nanopore 10 in the membrane device of FIG. 5.

FIG. 7 is a sectional view after forming the nanopore 10 in the membrane device of FIG. 5. As a method of forming the nanopore 10, a method similar to that described in the first embodiment can be used.

Figure 8:
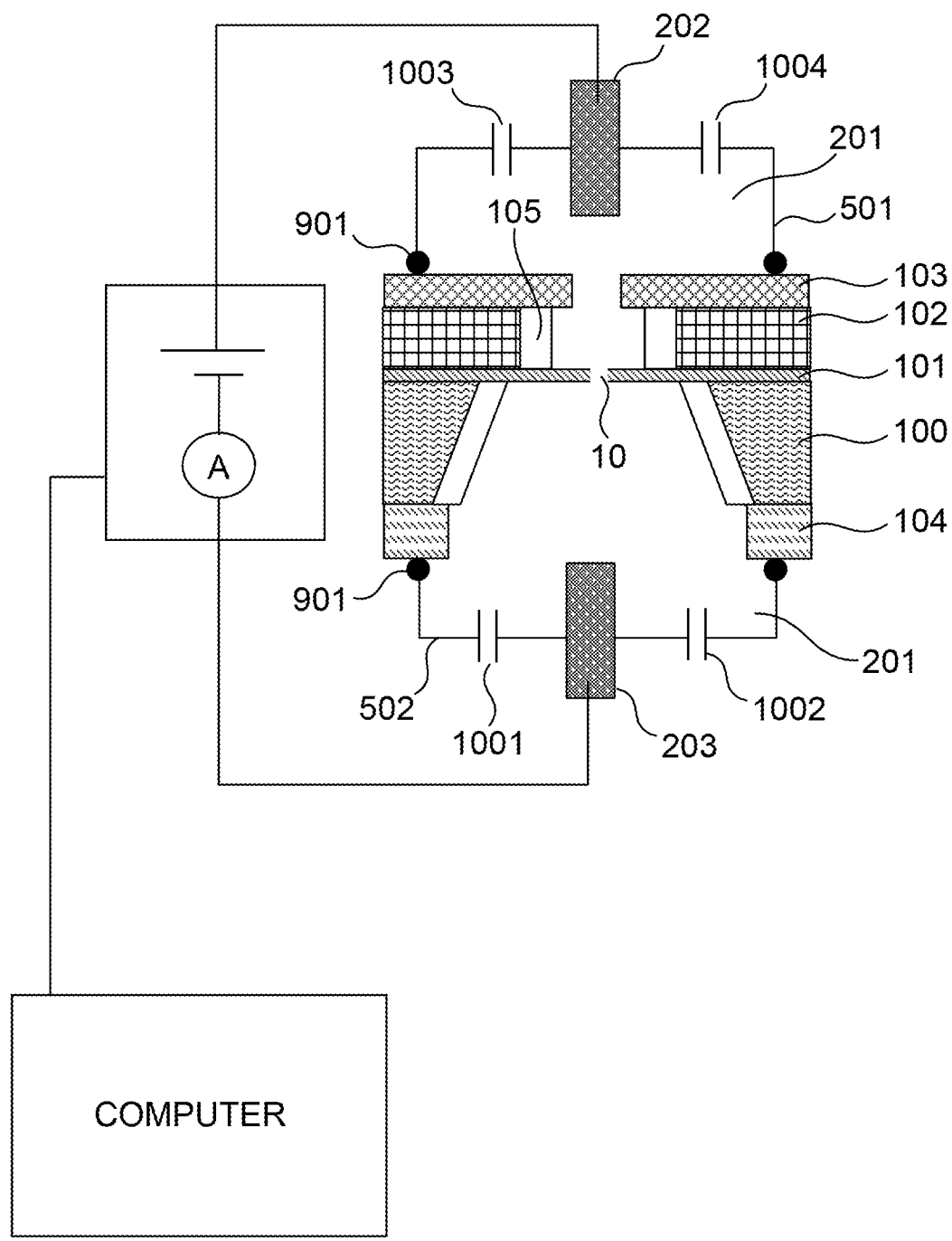
FIG. 8 is a configuration diagram of a measuring device provided with the membrane device illustrated in FIG. 7.

FIG. 8 is a configuration diagram of a measuring device provided with the membrane device illustrated in FIG. 7. Although the structure of the membrane device is replaced with that of FIG. 7, the other configuration is the same as that of FIG. 3.

In the second embodiment, the side wall of the hole provided in the Si substrate 100 is also oxidized so as to form the $SiO_2$ film 106. Therefore, when comparing with the first embodiment, electrostatic capacity between the electrode 202 and the electrode 203 is decreased. This is because the larger the amount of the insulating film present between the electrode 202 and the electrode 203, the lower the dielectric constant between the electrodes. When the electrostatic capacity between the electrodes is lowered, the noise due to the electrostatic capacity is decreased, so that the noise when measuring the ion current passing through the nanopore 10 is decreased. Therefore, it is possible to detect the ion current more accurately by more decreasing the noise than that of the first embodiment.

Third Embodiment

Figure 9:
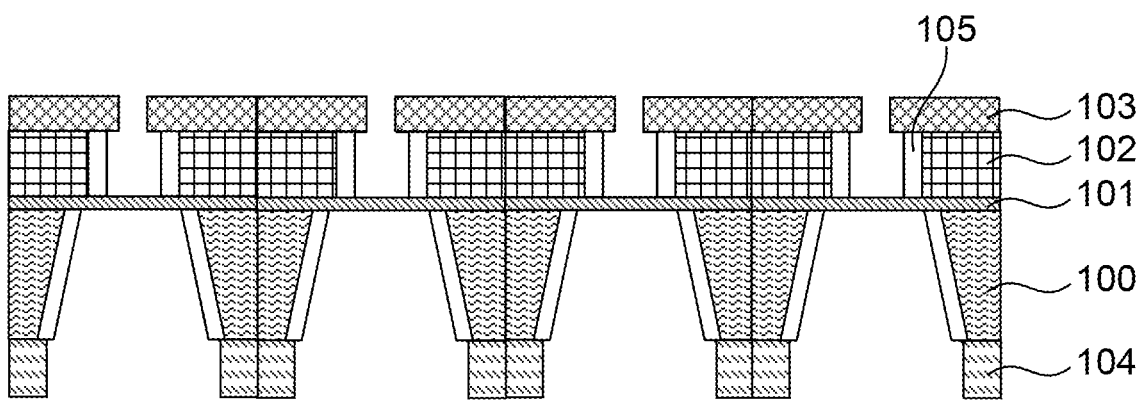
FIG. 9 is a sectional view of a membrane device according to a third embodiment of the present invention.

FIG. 9 is a sectional view of a membrane device according to a third embodiment of the present invention. The membrane device according to the third embodiment has an array-like configuration in which a plurality of structures of the membrane device (hereinafter, it may be referred to as a measuring unit) described in the second embodiment are periodically arranged on the same chip. The number of measuring units is optional. The membrane devices described in the first embodiment can be disposed in an array. In the following description, the structure of FIG. 9 is assumed.

Figure 10:
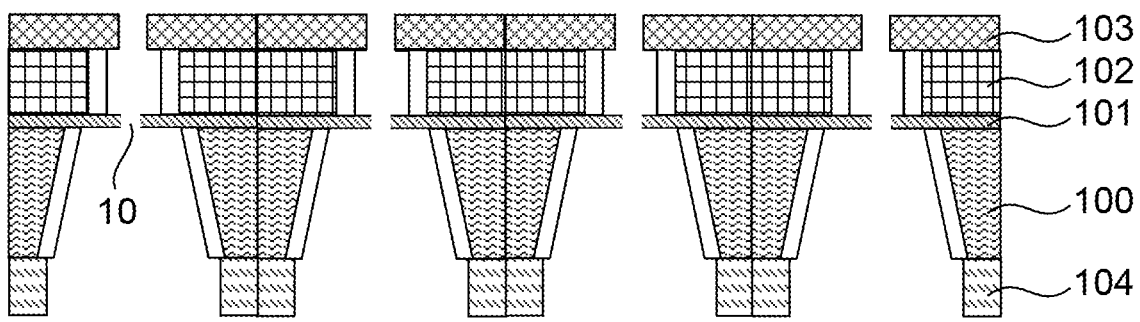
FIG. 10 is a sectional view after forming a nanopore 10 in the membrane device of FIG. 9.

FIG. 10 is a sectional view after forming the nanopore 10 in the membrane device of FIG. 9. As a method of forming the nanopore 10, a method similar to that described in the first embodiment can be used.

Figure 11:
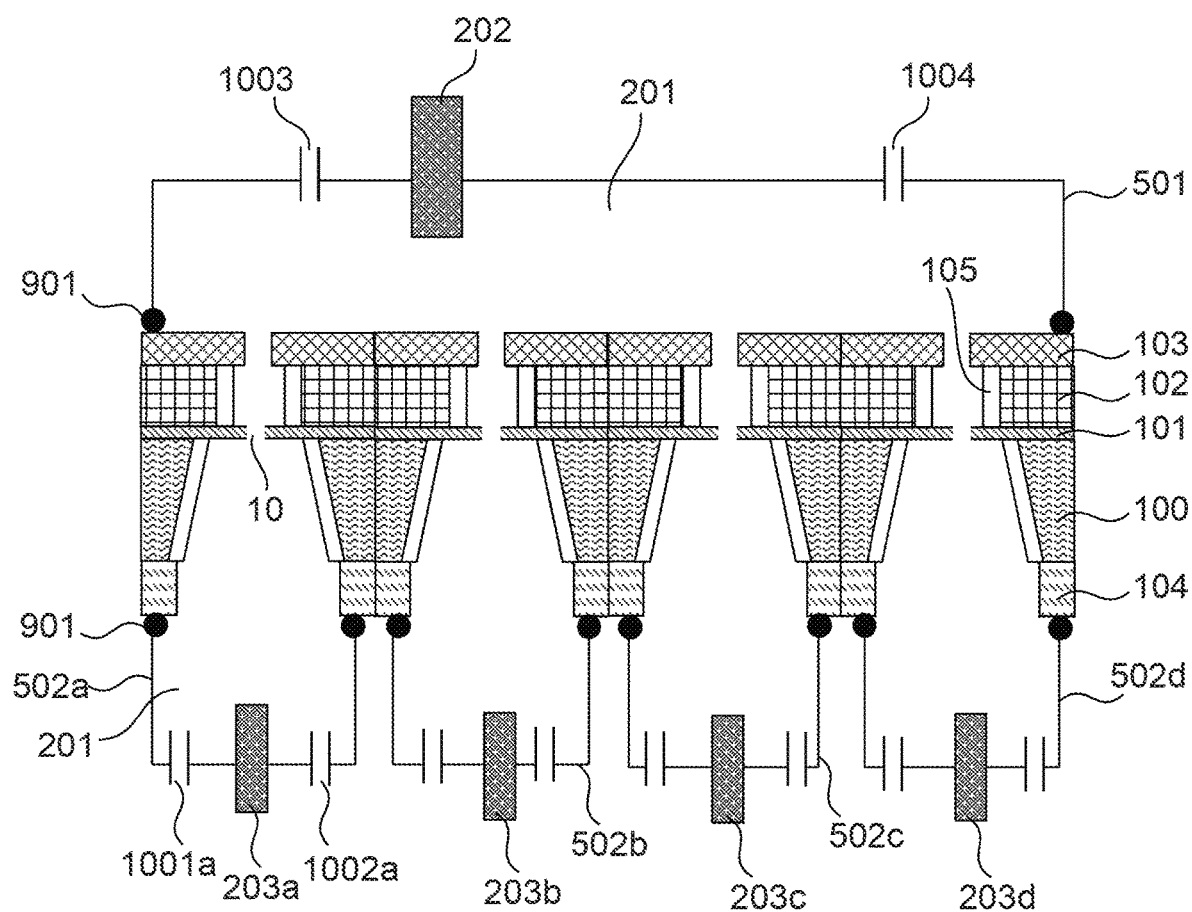
FIG. 11 is a configuration diagram of a measuring device provided with the membrane device illustrated in FIG. 10.

FIG. 11 is a configuration diagram of a measuring device provided with the membrane device illustrated in FIG. 10. The first chamber 501 collectively accommodates a plurality of measuring units by collectively covering the holes on the SiN film 103 included in each of the plurality of measuring units. The second chamber 502 is provided for each measuring unit and is separately provided so that the aqueous solution therein does not mix. The electrode 203 (i.e., 203a, 203b, 203c, 203d) is provided for each second chamber 502 (i.e., 502a, 502b, 502c, 502d). In order to distinguish the second chamber 502 and the electrode 203, which correspond to each measuring unit, from each other, subscripts of letters (i.e., a, b, c, d) are attached in FIG. 11. Each of the electrodes has an inlet and an outlet, such as inlet 1001a and outlet 1002a of electrode 203a. Other configurations are the same as those in FIG. 3.

Figure 12:
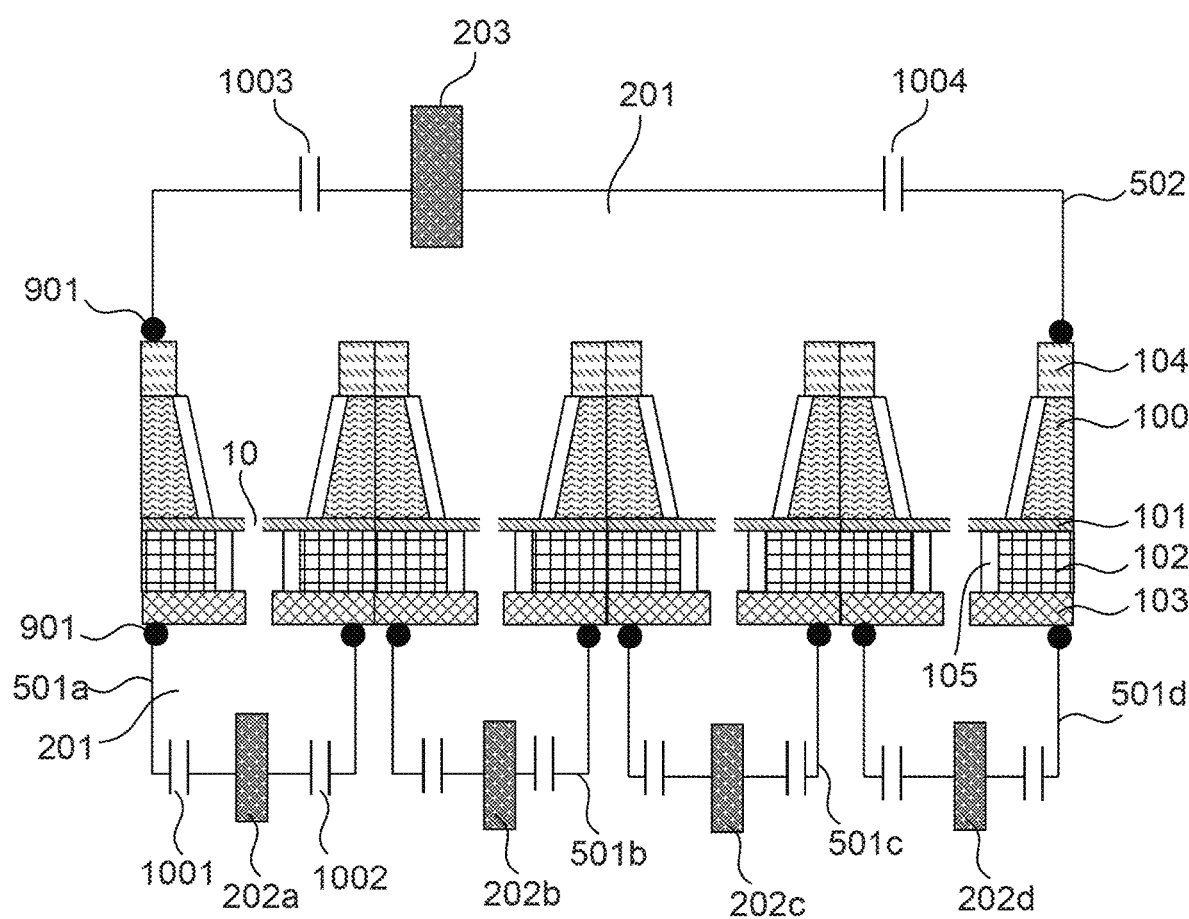
FIG. 12 is another configuration diagram of a measuring device provided with the membrane device illustrated in FIG. 10.

FIG. 12 is another configuration diagram of a measuring device provided with the membrane device illustrated in FIG. 10. The second chamber 502 collectively accommodates a plurality of measuring units by collectively covering the holes on the SiN film 104 included in each of the plurality of measuring units. The first chamber 501 is provided for each measuring unit and is separately provided so that the aqueous solution therein does not mix. The electrode 202 (i.e., 202a, 202b, 202c, 202d) is provided for each first chamber 501 (i.e., 501a, 501b, 501c, 501d). In order to distinguish the first chamber 501 and the electrode 202, which correspond to each measuring unit, from each other, subscripts of letters (i.e., a, b, c, d) are attached in FIG. 12. Other configurations are the same as those in FIG. 3.

The configuration in FIG. 12 has the following advantages compared with the configuration in FIG. 11. In FIG. 12, as compared with FIG. 11, the surface of the membrane device on the side closer to the electrode 202 is separated for each measuring unit by the first chamber 501. The electrostatic capacity between the electrodes (between 203 and 202a, between 203 and 202b, between 203 and 202c, and between 203 and 202d) depends mainly on the liquid contact area of the surface of the membrane device closer to the electrode 202, and as the liquid contact area is decreased, the electrostatic capacity between the electrodes is also decreased. Therefore, as compared with the configuration in FIG. 11, the configuration in FIG. 12 has an effect of decreasing the noise because the electrostatic capacity between the electrodes used for measurement is smaller.

In the third embodiment, since it is possible to simultaneously measure four nanopores 10, it is advantageous that the measurement throughput is quadrupled compared with that of a single nanopore measurement. In general, when the number of measuring units is increased, the throughput of the measurement is improved by that much.

Fourth Embodiment

In the fourth embodiment of the present invention, a method of manufacturing the membrane device described in the second embodiment will be described. The names of the respective parts are the same as those described in the first and second embodiments.

Figure 13:
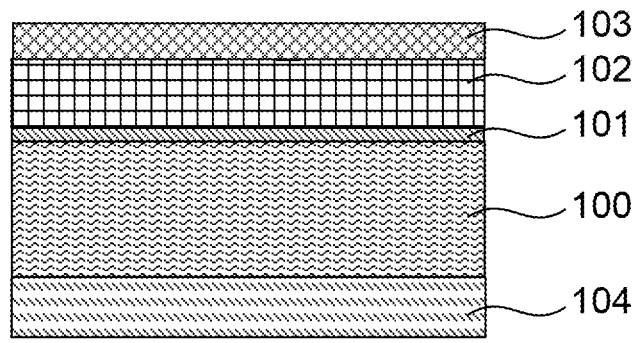
FIG. 13 is a sectional view illustrating a step of stacking each layer.

FIG. 13 is a sectional view illustrating a step of stacking each film. The SiN film 101, the poly-Si film 102, and the SiN film 103 are stacked in this order on the Si substrate 100. The SiN film 104 is stacked on the back surface of the Si substrate 100. For example, the thickness of the SiN film 101 is 3 nm, the thickness of the poly-Si film 102 is 150 nm, the thickness of the SiN film 103 is 100 nm, the thickness of the SiN film 104 is 100 nm, and the Si substrate 100 is 725 um.

Figure 14:
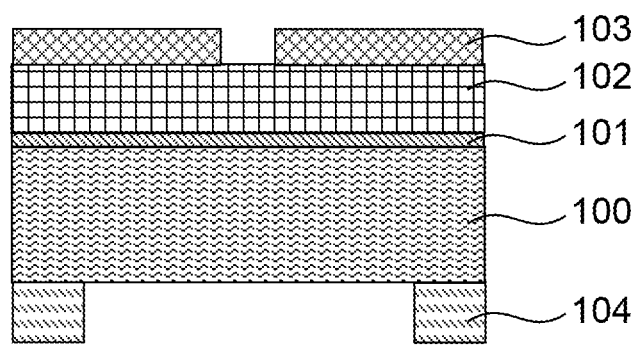
FIG. 14 illustrates a step of providing a through hole on a SiN film 103 and a SiN film 104.

FIG. 14 illustrates a step of providing a through hole on the SiN film 103 and the SiN film 104. For example, holes having an opening diameter of about 100 nm are formed in part of the SiN film 103 by dry etching. For example, rectangular holes with a size of 1038 um in length and 1038 um in width are formed in a part of the SiN film 104 by dry etching.

Figure 15:
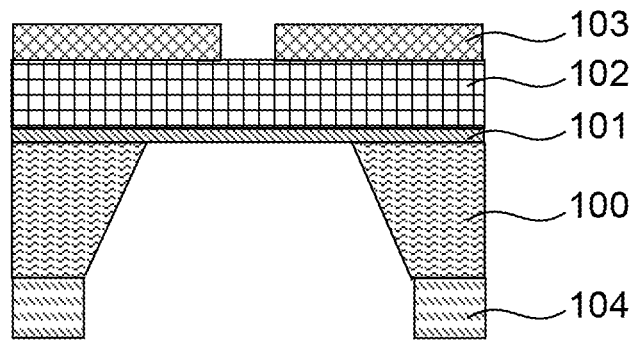
FIG. 15 illustrates a step of providing the through hole on a Si substrate 100.

FIG. 15 illustrates a step of providing the through hole on the Si substrate 100. The back surface of the Si substrate 100 is etched using a TMAH solution by setting the SiN film 104 as a mask. After etching, a region (corresponding to a membrane region) in which the SiN film 101 is exposed, approximately 80 um in length and 80 um in width, is formed. At the time of etching, by protecting the surface side of the membrane device with an organic protective film or the like resistant to the TMAH solution, it is possible to prevent the surface side of the membrane device from being etched. When the etching is completed, the organic protective film on the surface of the Si substrate 100 is removed with acetone or the like.

Figure 16:
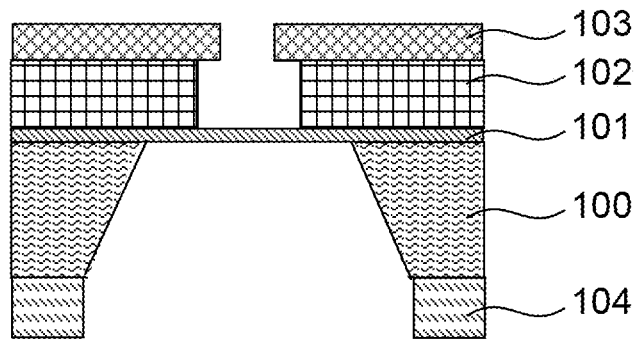
FIG. 16 illustrates a step of providing the through hole on a poly-Si film 102.

FIG. 16 illustrates a step of providing the through hole on the poly-Si film 102. A part of the poly-Si film 102 is etched using the KOH aqueous solution by using SiN film 103 as a mask. Accordingly, a membrane region formed of the SiN film 101 is formed. For example, when etching is performed at room temperature for about 20 minutes, the diameter of the pore formed in the poly-Si film 102 is about 600 nm.

Figure 17:
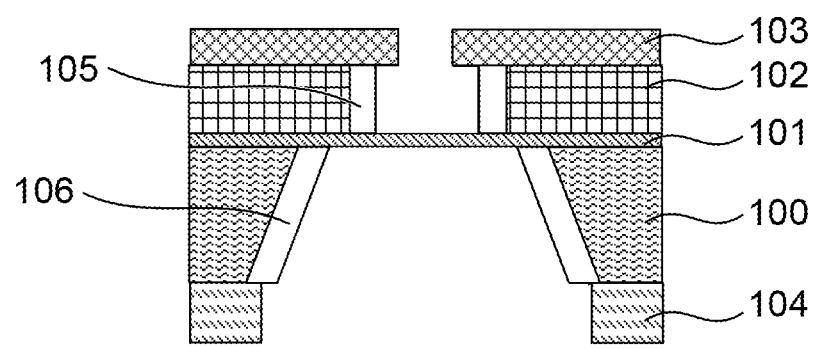
FIG. 17 illustrates a step of forming a $SiO_2$ film 105 and a $SiO_2$ film 106.

FIG. 17 illustrates a step of forming the $SiO_2$ film 105 and the $SiO_2$ film 106. The oxidation in an oxygen atmosphere is performed, for example, at 900° C. to 950° C. for about ten hours so as to form the $SiO_2$ film 105 and the $SiO_2$ film 106 having a thickness of about 100 nm. Since SiN is difficult to be oxidized, only the surface on which Si is exposed to oxygen atmosphere is oxidized, and the surface where SiN is exposed is hardly oxidized.

Through the above steps, the membrane device according to the second embodiment can be manufactured. Since the through holes are not provided in the poly-Si film 102 when etching the Si substrate 100, the above-described steps are advantageous in that the Si substrate 100 can be etched in a state where the strength of the poly-Si film 102 is sufficiently maintained.

Fifth Embodiment

In the fifth embodiment of the present invention, a method of manufacturing the membrane device described in the first embodiment will be described. The names of the respective parts are the same as those described in the first and second embodiments.

Figure 18:
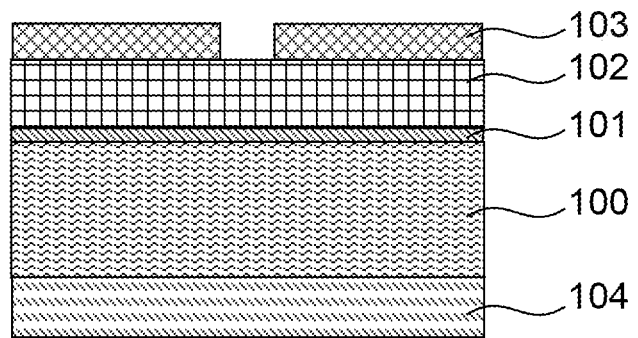
FIG. 18 illustrates a step of providing the through hole on the SiN film 103.

FIG. 18 illustrates a step of providing the through hole on the SiN film 103. After the step described in FIG. 13, for example, holes having an opening diameter of about 100 nm are formed in part of the SiN film 103 by dry etching.

Figure 19:
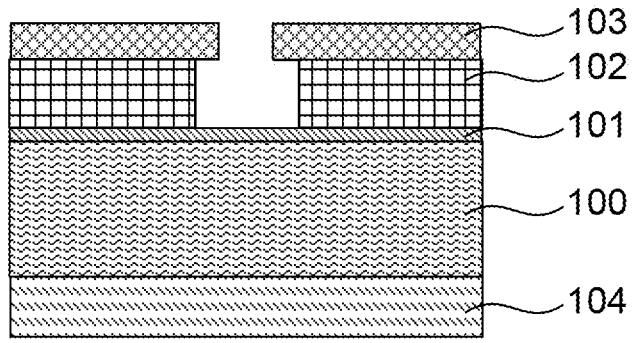
FIG. 19 illustrates a step of providing the through hole on the poly-Si film 102.

FIG. 19 illustrates a step of providing the through hole on the poly-Si film 102. Holes are formed in a part of the poly-Si film 102 using the KOH aqueous solution by using SiN film 103 as a mask. For example, when etching is performed at room temperature for about 20 minutes, the diameter of the pore formed in the poly-Si film 102 is about 600 nm.

Figure 20:
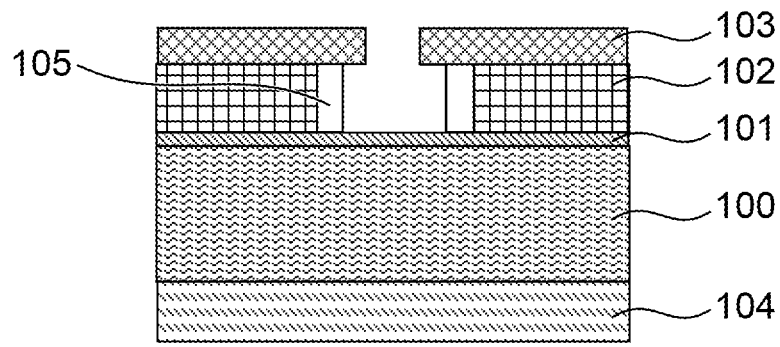
FIG. 20 illustrates a step of forming the $SiO_2$ film 105.

FIG. 20 illustrates a step of forming the $SiO_2$ film 105. The oxidation in an oxygen atmosphere is performed, for example, at 900° C. to 950° C. for about ten hours so as to form the $SiO_2$ film 105 having a thickness of about 100 nm. Since SiN is difficult to be oxidized, only the surface on which Si is exposed to oxygen atmosphere is oxidized, and the surface where SiN is exposed is hardly oxidized.

Figure 21:
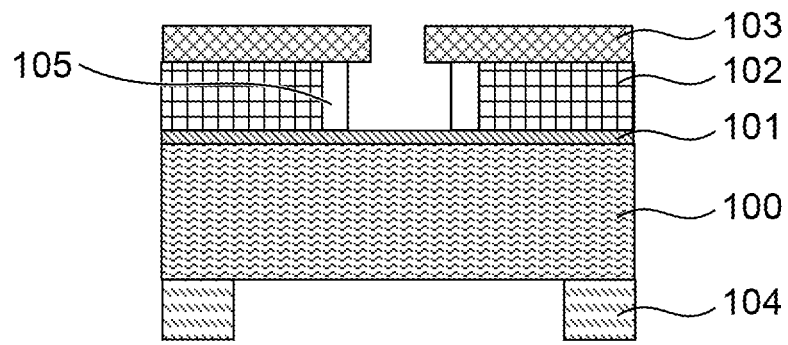
FIG. 21 illustrates a step of providing the through hole on the SiN film 104.

FIG. 21 illustrates a step of providing the through hole on the SiN film 104. For example, rectangular holes with a size of 1038 um in length and 1038 um in width are formed in a part of the SiN film 104 by dry etching.

Figure 22:
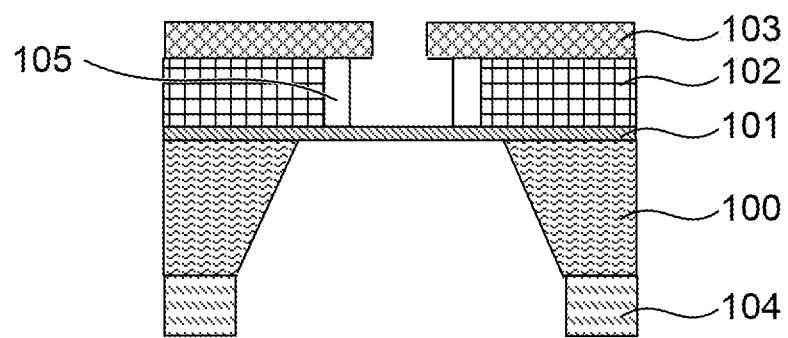
FIG. 22 illustrates a step of providing the through hole on the Si substrate 100.

FIG. 22 illustrates a step of providing the through hole on the Si substrate 100. The back surface of the Si substrate 100 is etched using a TMAH solution by setting the SiN film 104 as a mask. After etching, a region (corresponding to a membrane region) in which the SiN film 101 is exposed, approximately 80 um in length and 80 um in width, is formed. At the time of etching, by protecting the surface side of the membrane device with an organic protective film or the like resistant to the TMAH solution, it is possible to prevent the surface side of the membrane device from being etched. When the etching is completed, the organic protective film on the surface of the Si substrate 100 is removed with acetone or the like.

Through the above steps, the membrane device according to the first embodiment can be manufactured. In the membrane device according to the first embodiment, the surface of the Si substrate 100 is not covered with the $SiO_2$ film 106, but the frequency of the nanopore clogging phenomenon is considered to be very low. This is because the distance from the nanopore 10 to the edge of the Si substrate 100 is long (about 40 μm in the fifth embodiment), and thus the probability that DNA in the vicinity of the nanopore 10 interacts with the Si substrate 100 is very low. Therefore, even when only the side wall of the hole included in the poly-Si film 102 is covered with the $SiO_2$ film 105, the frequency of the nanopore clogging phenomenon can be greatly decreased.

Sixth Embodiment

In the membrane device described in the first to fifth embodiments, when the surface of the poly-Si film 102 is covered with an insulating film other than the $SiO_2$ film 105, the frequency of the nanopore clogging phenomenon can be decreased similar to the first to fifth embodiments. For example, it is conceivable to cover with a SiN film. Specifically, when the side wall of the hole in the poly-Si film 102 is annealed in an atmosphere of $NH_3$ and thus nitrided, it is possible to set the side wall surface of the poly-Si film 102 as a SiN film. For example, annealing may be performed at 1050° C. for 60 seconds in the atmosphere of $NH_3$. Due to the annealing in an atmosphere of $NH_3$, the thickness of the SiN film 101 is hardly changed. Therefore, the spatial resolution after forming the nanopore 10 is about the same as the spatial resolution of the nanopore sensor disclosed in NPTL 1.

Simultaneously with the annealing of the side wall of the poly-Si film 102 in an atmosphere of $NH_3$, the surface of the Si substrate 100 may be also annealed in an atmosphere of $NH_3$, so that the surface of the Si substrate 100 can also be covered with the SiN film. When the surface of the Si substrate 100 is also covered with the SiN film, the electrostatic capacity between the electrodes is decreased at the time of measuring the ion current passing through the nanopore 10. Therefore, measurement noise can be suppressed low.

Regarding Modification Example of the Present Invention

Regarding the method of forming the nanopore, as described in the background art, there are several methods, which are widely and commonly spread. Therefore, as a form of the product of the invention, it is conceivable to provide the user with a membrane device before the nanopore is formed, and the provided user forms a nanopore having a size suitable for the intended measurement. Also, transitioning to measurement of an object using the nanopore immediately after forming the nanopore by a user is effective in decreasing adherence of foreign matters to the membrane device, and it is considered to realize more accurate measurement.

Alternatively, a membrane device in which nanopores have already been formed is provided to the user, and the user may perform a desired measurement using the membrane device. In this case, it is possible to save time for the user to form the nanopores.

In the above-described embodiments, the examples of determining the base sequence of DNA have been described. However, the present invention can also be used for identification and structure determination of various molecules other than DNA, and measurement of the number of molecules passing through the nanopores.

REFERENCE SIGNS LIST

10 NANOPORE
100 Si substrate
101 SiN FILM
102 POLY-Si FILM
103 SiN FILM
104 SiN FILM
105 $SiO_2$ FILM
106 $SiO_2$ FILM
201 AQUEOUS SOLUTION
202 ELECTRODE
203 ELECTRODE
501 FIRST CHAMBER
502 SECOND CHAMBER
901 O-RING
1001 INLET
1002 OUTLET
1003 INLET
1004 OUTLET

The invention claimed is:

1. A membrane device comprising:
   a Si substrate;
   a membrane disposed on the Si substrate; and
   a semiconductor layer which is formed of polysilicon or amorphous silicon and is disposed on the membrane,
   wherein the semiconductor layer includes a first hole penetrating to a depth reaching the membrane,
   wherein the Si substrate includes a second hole penetrating to a depth reaching the membrane,
   wherein the membrane is disposed in a position where the first hole and the second hole are separated from each other by the membrane,
   wherein a first insulating film is disposed on a side wall of the first hole,
   wherein a third insulating film formed of $SiO_2$ or SiN is disposed on a side wall of the second hole,
   wherein the membrane has a nanopore that transmits a DNA molecule,
   wherein the semiconductor layer and the nanopore are placed at relative positions where an interference effect occurs between the semiconductor layer and the DNA molecule clogging the DNA molecule within the nanopore when the DNA molecule passes through the nanopore, and
   wherein the first insulating film has an effect that decreases the interference effect.

2. The membrane device according to claim 1,
   wherein the membrane device includes a second insulating film disposed on the semiconductor layer, and
   wherein the second insulating film includes a third hole communicating with the first hole.

3. The membrane device according to claim 2,
   wherein the second insulating film is formed of $SiO_2$ or SiN.

4. The membrane device according to claim 1,
   wherein the first insulating film is formed of $SiO_2$ or SiN.

5. The membrane device according to claim 1,
   wherein the membrane is formed of SiN.

6. The membrane device according to claim 1,
   wherein the membrane includes a third hole that causes the first hole and the second hole to communicate with each other.

7. The membrane device according to claim 1,
   wherein a thickness of the first insulating film is 5 nm or more.

8. The membrane device according to claim 1,
   wherein a thickness of the first insulating film is 10 nm or more.

9. A measuring device that measures physical properties of a sample, the measuring device comprising:
   a measuring unit that accommodates the sample;
   first and second chambers;
   a first electrode that applies a voltage to an aqueous solution accommodated in the first chamber; and
   a second electrode that applies a voltage to an aqueous solution accommodated in the second chamber,
   wherein the measuring unit includes
      a Si substrate,
      a membrane disposed on the Si substrate, and
      a semiconductor layer which is formed of polysilicon or amorphous silicon and is disposed on the membrane,
   wherein the semiconductor layer includes a first hole penetrating to a depth reaching the membrane,
   wherein the Si substrate includes a second hole penetrating to a depth reaching the membrane,
   wherein the membrane is disposed in a position where the first hole and the second hole are separated from each other by the membrane, and
   wherein a first insulating film is disposed on a side wall of the first hole,
   wherein a third insulating film formed of $SiO_2$ or SiN is disposed on a side wall of the second hole,
   wherein the membrane has a nanopore that transmits a DNA molecule,
   wherein the semiconductor layer and the nanopore are placed at relative positions where an interference effect occurs between the semiconductor layer and the DNA molecule clogging the DNA molecule within the nanopore when the DNA molecule passes through the nanopore, and wherein the first insulating film has an effect that decreases the interference effect.

10. The measuring device according to claim 9, further comprising a plurality of the measuring units,
wherein the second chamber is formed so as to collectively cover the second hole included in each of the plurality of the measuring units, and
wherein the first chamber and the first electrode are provided for each of the measuring units.

11. A method of manufacturing a membrane device, the method comprising:
stacking a membrane on a Si substrate;
stacking a semiconductor layer formed of polysilicon or amorphous silicon on the membrane;
forming a first hole penetrating to a depth reaching the membrane on the semiconductor layer; and
forming a second hole penetrating to the depth reaching the membrane on the Si substrate,
wherein the membrane is disposed in a position where the first hole and the second hole are separated from each other by the membrane,
the method further comprising forming a first insulating film on a side wall of the first hole,
wherein a third insulating film formed of $SiO_2$ or SiN is disposed on a side wall of the second hole,
wherein the membrane has a nanopore that transmits a DNA molecule,
wherein the semiconductor layer and the nanopore are placed at relative positions where an interference effect occurs between the semiconductor layer and the DNA molecule clogging the DNA molecule within the nanopore when the DNA molecule passes through the nanopore, and
wherein the first insulating film has an effect that decreases the interference effect.

12. A membrane device comprising:
a Si substrate;
a membrane disposed on the Si substrate; and
a semiconductor layer which is formed of polysilicon or amorphous silicon and is disposed on the membrane,
wherein the semiconductor layer includes a first hole penetrating to a depth reaching the membrane,
wherein the Si substrate includes a second hole penetrating to a depth reaching the membrane,
wherein the membrane is disposed in a position where the first hole and the second hole are separated from each other by the membrane,
wherein a first insulating film is disposed on a side wall of the first hole,
wherein the first insulating film is formed of $SiO_2$, and
wherein the membrane is formed so that a composition of the membrane continuously varies from SiN to $SiO_2$ from a center toward a surface in a thickness direction.

13. A membrane device comprising:
a Si substrate;
a membrane disposed on the Si substrate; and
a semiconductor layer which is formed of polysilicon or amorphous silicon and is disposed on the membrane,
wherein the semiconductor layer includes a first hole penetrating to a depth reaching the membrane,
wherein the Si substrate includes a second hole penetrating to a depth reaching the membrane,
wherein the membrane is disposed in a position where the first hole and the second hole are separated from each other by the membrane,
wherein a first insulating film is disposed on a side wall of the first hole, and
wherein the membrane is formed of any one of $HfO_2$, HfAlOx, ZrAlOx, $Ta_2O_5$, SiC, SiCN, a carbon film, and a compound thereof.

* * * * *